(12) United States Patent
DiSanzo et al.

(10) Patent No.: US 9,863,898 B2
(45) Date of Patent: Jan. 9, 2018

(54) HIGH TEMPERATURE SIMULATED DISTILLATION

(71) Applicants: Frank P. DiSanzo, Cherry Hill, NJ (US); Howard J. Freund, Neshanic Station, NJ (US); Edward A. Moy, Woodbury Heights, NJ (US)

(72) Inventors: Frank P. DiSanzo, Cherry Hill, NJ (US); Howard J. Freund, Neshanic Station, NJ (US); Edward A. Moy, Woodbury Heights, NJ (US)

(73) Assignee: EXXONMOBILE RESEARCH AND ENGINEERING COMPANY, Annandale, NJ (US)

( * ) Notice: Subject to any disclaimer, the term of this patent is extended or adjusted under 35 U.S.C. 154(b) by 522 days.

(21) Appl. No.: 14/556,369

(22) Filed: Dec. 1, 2014

(65) Prior Publication Data

US 2015/0198545 A1    Jul. 16, 2015

Related U.S. Application Data

(60) Provisional application No. 61/917,536, filed on Dec. 18, 2013.

(51) Int. Cl.
*G01N 25/12* (2006.01)
*G01N 25/08* (2006.01)
(Continued)

(52) U.S. Cl.
CPC .......... *G01N 25/08* (2013.01); *G01N 25/14* (2013.01); *G01N 30/12* (2013.01); *G01N 30/30* (2013.01);
(Continued)

(58) Field of Classification Search
CPC ......... G01N 25/02; G01N 25/08; G01N 25/12
See application file for complete search history.

(56) References Cited

U.S. PATENT DOCUMENTS 3,527,567 A * 9/1970 O'Neal, Jr. ............ G01N 30/30
422/78
3,574,549 A * 4/1971 Eggertstein .............. G01N 7/14
374/54
(Continued)

FOREIGN PATENT DOCUMENTS

| EP | 2629092 A2 | 8/2013 |
|---|---|---|
| JP | 56054352 A * | 5/1981 |
| WO | 2009051742 A1 | 4/2009 |

OTHER PUBLICATIONS

PCT Application No. PCT/US2014/068115, Communication from the International Searching Authority, International Search Report and Written Opinion, Form PCT/ISA/210 and Form PCT/ISA/237, dated Feb. 9, 2015, 13 pages.

(Continued)

*Primary Examiner* — Gail Kaplan Verbitsky
(74) *Attorney, Agent, or Firm* — Glenn T. Barrett; Andrew T. Ward

(57) ABSTRACT

Systems and methods for determining a boiling point distribution of a sample include controlling the rates of temperature increase for a column and an injection port. An analyzer includes a column having a column heating element and an injection port having an injection port heating element. The temperature of the column can be increased at a first rate, and a temperature of the injection port can be increased at a second rate. The first and second rates are selected such that the temperature of the injection port is within about five to fifteen degrees Celsius of the tempera- (Continued)

ture of the column when the temperature of the injection port reaches a target temperature of minimal thermal decomposition.

20 Claims, 11 Drawing Sheets

(51) Int. Cl.
    *G01N 25/14*    (2006.01)
    *G01N 30/30*    (2006.01)
    *G01N 33/28*    (2006.01)
    *G01N 30/12*    (2006.01)
    *G01N 30/88*    (2006.01)

(52) U.S. Cl.
    CPC ......... *G01N 30/88* (2013.01); *G01N 33/2823* (2013.01); *G01N 2030/127* (2013.01); *G01N 2030/3076* (2013.01); *G01N 2030/8854* (2013.01)

(56) References Cited

U.S. PATENT DOCUMENTS

| | | | | |
|---|---|---|---|---|
| 4,024,752 A * | 5/1977 | Orlando | ................. | G01N 25/08 374/27 |
| 4,757,023 A * | 7/1988 | Trestianu | ............... | G01N 30/88 422/54 |
| 4,872,334 A * | 10/1989 | Watanabe | .............. | G01N 30/32 422/89 |
| 5,792,663 A * | 8/1998 | Fry | .......................... | B01D 1/22 159/13.1 |
| 6,790,669 B1 * | 9/2004 | Pfeiffer | .................. | G01N 30/88 436/161 |
| 9,176,102 B2 * | 11/2015 | Wang | ................... | G01N 30/463 |
| 2007/0060713 A1 * | 3/2007 | Gracey | ................... | C07C 69/60 525/438 |
| 2009/0057196 A1 * | 3/2009 | Leta | ........................ | C10B 55/00 208/85 |
| 2011/0209525 A1 * | 9/2011 | Wang | ................... | G01N 30/463 73/23.35 |
| 2012/0138508 A1 * | 6/2012 | Okabe | ....................... | C10L 1/08 208/15 |
| 2013/0218481 A1 * | 8/2013 | Green | .................... | G01N 30/88 702/30 |
| 2014/0231641 A1 * | 8/2014 | Qian | ................... | H01J 49/0027 250/282 |
| 2014/0249338 A1 * | 9/2014 | Roussis | ..................... | A23D 9/00 585/24 |

OTHER PUBLICATIONS

L. Carbognani, J. Carbognani Araivibarri, H. Molero and P. Pereira-Almao, "High Temperature Simulated Distillation of Bitumen Fractions with Open Tubular Capillary Columns Depleted in Silicone/Siloxane Stationary Phases", Energy & Fuels, vol. 27, No. 4., Mar. 9, 2013, pp. 2033-2041.

L. Cargognani, J. Lubkowiz, M.F. Gonzales and P. Pereira-Almao, High Temperature Simulated Distillation of Athabasca Vacuum Residue Fractions, Bimodal Distributions and Evidence for Secondary 'On-Column' Cracking of Heavy Hydrocarbons, Energy & Fuels, 2007, 21, pp. 2831-2839.

ASTM D7169, downloaded from http://emreapp2.na.xom.com/computingiscripts/ihs.asp?reqType=STDS on Feb. 16, 2015.

* cited by examiner (GC Oven=Column)

HIGH TEMPERATURE SIMULATED DISTILLATION

CROSS-REFERENCE TO RELATED APPLICATIONS

This application claims priority to U.S. Provisional Application Ser. No. 61/917,536 filed Dec. 18, 2013, herein incorporated by reference in its entirety.

BACKGROUND OF THE INVENTION

Field of the Invention

The disclosed subject matter of this application is generally related to methods and system for high temperature simulated distillation. Particularly, the present application relates to systems and methods for determining a boiling point distribution of a sample containing high boiling petroleum compounds, such as a petroleum residua.

Description of Related Art

Simulated distillation using gas chromatography can be applied to high boiling point petroleum fractions, such as those containing residua, by extending the methodology to higher operating temperatures of the analyzer. This high temperature version of the technique is generally referred to as high temperature simulated distillation, or HT-Simdis. HT-Simdis is a relatively rapid technique when compared to conventional distillations, requires small sample sizes, and can be readily automated. HT-Simdis data can be used for development of improved processes for upgrading residua and other heavy petroleum fractions and for modeling such fractions.

HT-Simdis techniques generally employ analyzer temperatures of up to 430-450° C. Due to the use of such high temperatures, application of HT-Simdis to residua may be affected by thermal decomposition. In particular, thermal decomposition can affect the accuracy of the simulated distillation boiling point curve. Although thermal decomposition has been reported in the literature, no consensus solution has been reported on how to obtain optimum simulated distillation curves and apply to Model of Composition. Experts in the field use wide ranging operating conditions for the HT-simdis analyzers that lead to thermal decomposition since the problem is not well recognized or solved. The current international consensus test method organizations (e.g. ASTM, ISO etc.) do not provide a simulated distillation methodology to account for the potential problems caused by thermal decomposition. As such, there remains a need for methods and systems capable of applying HT-Simdis accounting for the effect of thermal decomposition.

SUMMARY OF THE INVENTION

The purpose and advantages of the subject matter of this application will be set forth in and apparent from the description that follows, as well as will be learned by practice of the disclosed subject matter. Additional advantages of the disclosed subject matter will be realized and attained by the method and apparatus particularly pointed out in the written description and claims hereof, as well as from the appended drawings.

In accordance with one aspect of the disclosed subject matters, methods for determining a boiling point distribution of a sample are provided. In one embodiment, the method includes providing an analyzer including a column having a column heating element and an injection port coupled to the column, the injection port having an injection port heating element. A sample can be introduced into the injection port. The temperature of the column can be raised at a first rate using the column heating element and the temperature of the injection port can be raised at a second rate using the injection port heating element. The first rate and the second rate can be selected such that the temperature of the column is within five to fifteen degrees Celsius of the temperature of the injection port when the temperature of the injection port reaches a target temperature. Preferably, the temperature is within five degrees Celsius.

The column can be, for example, a wall coated open tubular column or a packed column. The injection port can be, for example, a programmable temperature vaporizer. It is also contemplated that the injection port can be part of the column itself. The target temperature can be between about 380° C. and about 400° C. Preferably, the target temperature is about 390° C. The temperature of the injection port can be slightly higher than the temperature of the column when the temperature of the injection port reaches the target temperature or can be same as the column in the case whereby the injection port is part of the column. Ideally, the temperature of the injection port and the column should be identical when the target temperature is reached; however, due to thermal lags or accuracy of the readouts from the injection port and column temperature, for practical purposes the injection port can be within an approximately five to degrees Celsius so that material in the injection port does not lag behind in its elution. Where the sample is injected directly into the column, the column temperature is the main temperature that will reach the target temperature.

In accordance with embodiments of the disclosed subject matter, the first rate and second rate are adjusted such that when the column temperature reaches the target cut off temperature the injection port temperature is 15° C. or less above that of the column temperature. The first rate is greater than the second rate when the column and the injection port are separate components. The rates are the same when the injection port is part of the column. The starting temperature of the column can be lower than the starting temperature of the injection port.

The method disclosed herein can further include measuring a boiling point distribution of the sample. The boiling point distribution can be measured using, for example, a flame ionization detector.

In accordance with embodiments of the disclosed subject matter, the method can further include defining a cutoff temperature and selecting a first set of data associated with temperatures lower than the cutoff temperature to measure the boiling point of the sample. The cutoff temperature can be the target temperature or a temperature lower than the target temperature.

The sample can be, for example, a petroleum stream. In an exemplary embodiment, the method can further include constructing an initial estimate of a composition of the petroleum stream. This can be accomplished using, for example, mass spectrometry or a flame ionization detector. The initial estimate of composition can be a Heavy Hydrocarbon Model of Composition. A chromatogram can be created based on analysis of the sample.

The temperature of the injection port and the column can be increased above the target temperature of the column after the temperature of the injection port reaches the target temperature to a temperature sufficient to elute remaining portions of the sample. This can be done in order to clean the column and the injection port.

In accordance with another aspect of the disclosed subject matter, systems for determining a boiling point distribution of a sample are provided. The system can include an analyzer including a column having a column heating element and an injection port coupled to the column, an injection port having an injection port heating element. The analyzer is configured to raise a temperature of the column at a first rate using the column heating element, and to raise a temperature of the injection port at a second rate using the injection port heating element, wherein the first and second rates are selected such that the temperatures of the injection port is within five to fifteen degrees Celsius of the temperature of the column when the temperature of the column reaches a target temperature. The temperature of the injection port is preferably within five to ten degrees Celsius of the temperature of the column. The temperature of the injection port is more preferably within five degrees Celsius of the temperature of the column. The temperature of the injection port is more preferably equal to the temperature of the column. The analyzer may include one or more processors including one or more electronic circuits for implementing such functionality. Alternatively or additionally, the analyzer can include computer readable media storing instructions that, when implemented by the one or more processors, causes the one or more processors to carry out the temperature increases.

DETAILED DESCRIPTION OF THE PREFERRED EMBODIMENT

Overview

Generally, the disclosed subject matter is directed to a method for determining a boiling point distribution of a sample, the method comprising providing an analyzer including a column having a column heating element and an injection port coupled to the column, the injection port including an injection port heating element. The method further includes introducing a sample into injection port, raising the temperature of the column at a first rate using the column heating element, and raising the temperature of the injection port at a second rate using the injection port heating element. The first rate and the second rate are selected such that the temperature of the injection port is within approximately five to fifteen degrees Celsius of the temperature of the column when the temperature of column reaches a target temperature. The temperature of the injection port is preferably within five to ten degrees Celsius of the temperature of the column. The temperature of the injection port is more preferably within five degrees Celsius of the temperature of the column. The temperature of the injection port is more preferably equal to the temperature of the column. The first rate and the second may be equal rate if injection port is part of the column Additionally, a system is provided herein. The system generally includes an analyzer including a column comprising a column heating element and an injection port coupled to the column, the injection port comprising an injection port heating element. The analyzer is configured to raise a temperature of the column at a first rate using the column heating element, and to raise a temperature of the injection port at a second rate using the injection port heating element, wherein the first rate and the second rate are selected such that the temperature of the injection port is within five to fifteen degrees Celsius of the temperature of the column when the temperature of the column reaches a target temperature. The temperature of the injection port is preferably within five to ten degrees Celsius of the temperature of the column. The temperature of the injection port is more preferably within five degrees Celsius of the temperature of the column. The temperature of the injection port is more preferably equal to the temperature of the column.

Reference will now be made in detail to representative embodiments of the disclosed subject matter, examples of which are illustrated in the accompanying drawings. The methods and systems disclosed herein will be described in conjunction with each other for clarity.

Figure 1:
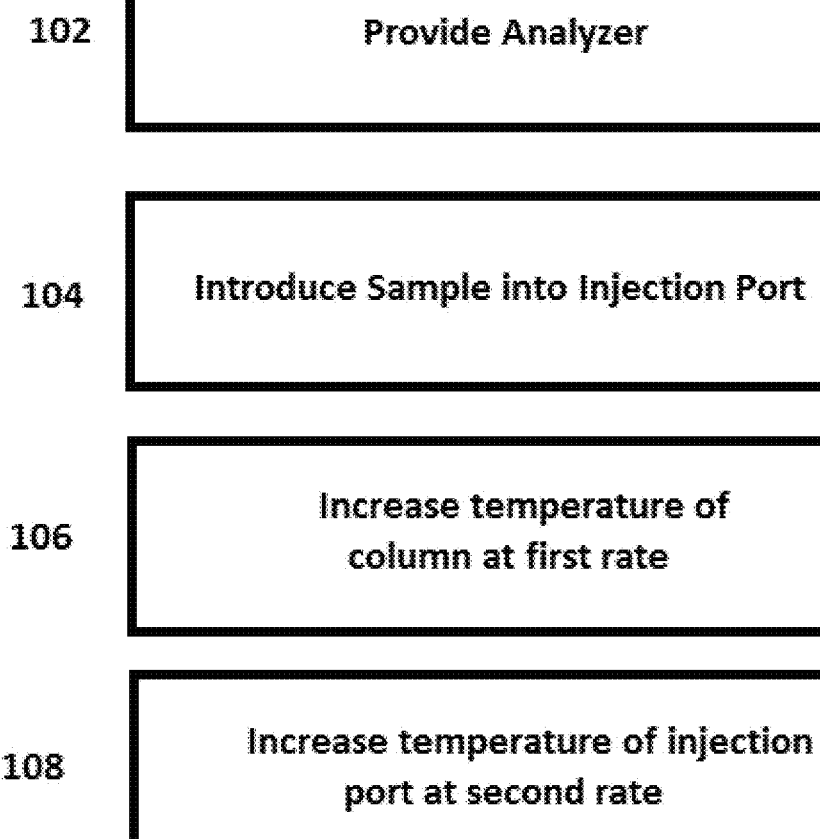
FIG. 1 is a flow chart generally describing a representative embodiment of a method for determining a boiling point distribution of a sample in accordance with the disclosed subject matter.
Figure 2:
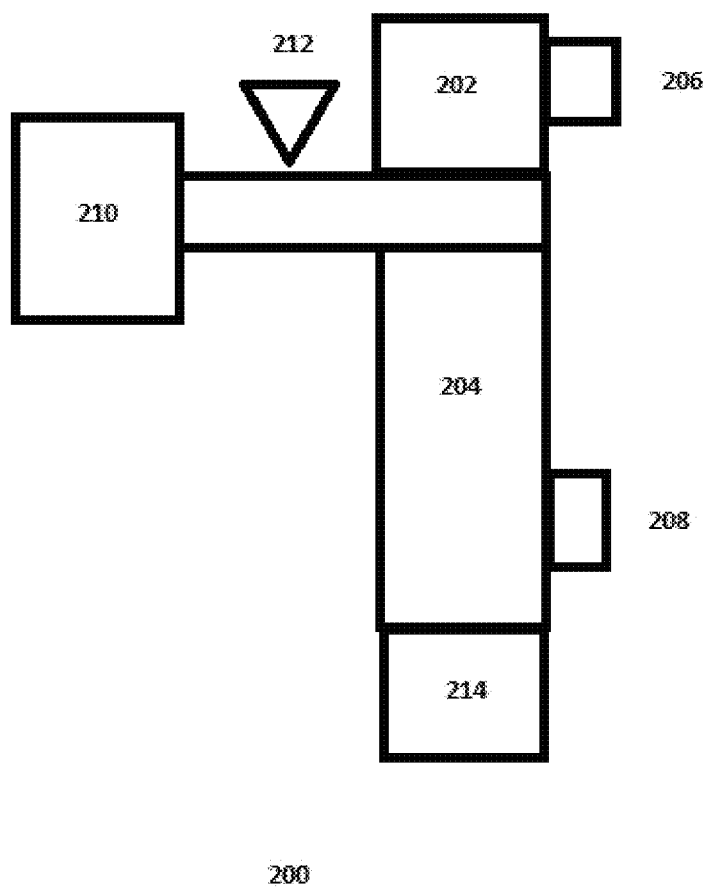
FIG. 2 is a schematic diagram of a representative analyzer in accordance with an embodiment of the disclosed subject matter.

With reference to FIG. 1, an exemplary method for determining a boiling point distribution of a sample is illustrated. As disclosed herein, the method includes providing an analyzer. A representative analyzer in accordance with the disclosed subject matter is shown in FIG. 2. The analyzer 200 generally includes an injection port 202 fluidly coupled to a column 204. The injection port 202 includes an injection port heating element 206. The column 204 also includes a column heating element 208. Injection port heating element 206 and column heating element 208 can be any suitable heating element as known in the art for its intended purpose. As embodied herein, the injection port 202 can be located proximate a first end of the column, such as proximate the front of the column.

Figure 3:
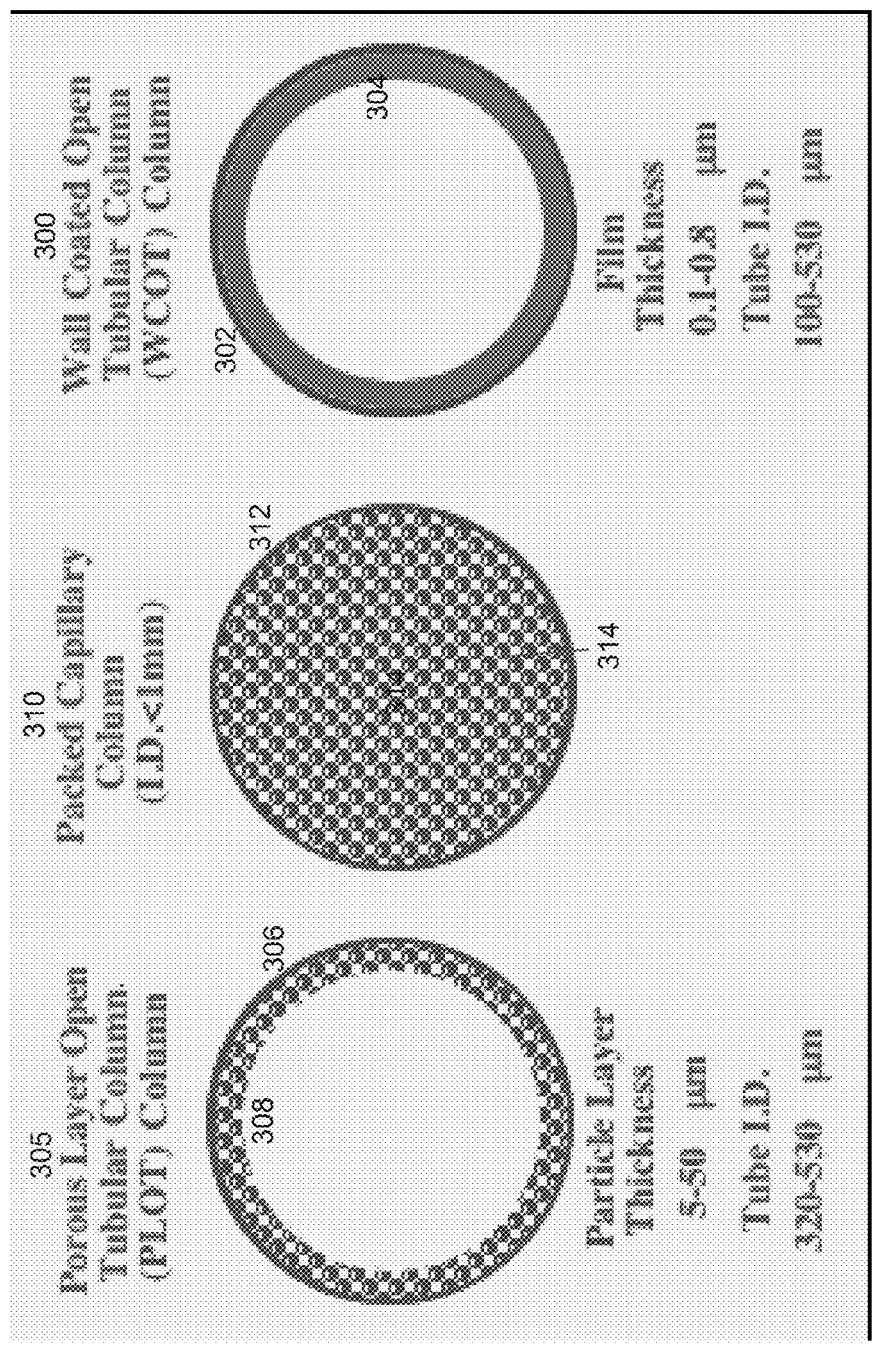
FIG. 3 is a schematic diagram illustrating a cross-section of representative columns suitable for use in an analyzer in accordance with embodiments of the disclosed subject matter.

A number of column configurations for use in gas chromatography are known and available. For example, the column can be a "wall coated open tubular column" or a "porous layer open tubular column." A cross-sectional view of an exemplary embodiment of a wall coated open tubular column in accordance with the disclosed subject matter is shown in FIG. 3. The wall coated open tubular column 300 includes an outer tube 302 and a stationary phase (e.g., film 304) disposed on the inner surface of the tube 302. The tube can be, for example, a thin fused-silica or metal capillary having a length between about 5 meters and about 100 meters, and an inner diameter between about 100 µm and about 530 µm. The stationary phase can be, for example, a polysiloxane (e.g. typically used in HT-simdis) such as polydimethyl siloxane or polyethylene glycol with a thickness of between about 0.1 µm and about 0.8 µm. Alternatively, outer tube 302 and film 304 can be made of any other suitable materials with suitable dimensions. Alternatively, and as noted above, the column for the method herein can be a "porous layer open tubular column 305," comprising an outer tube 306 having a stationary phase 308 in the form of a porous layer such as a porous polymer, along the inner diameter of the outer tube. The tube can have an inner diameter between about 320 µm and about 530 µm, and a stationary phase thickness of between about 5 µm and about 50 µm. Other column dimensions may be possible as dictated by the application.

In another embodiment of the disclosed subject matter, the column can be a packed column such as column 310 shown in FIG. 3. The packed column 310 includes an outer tube 312 with a stationary phase 314 packed inside the outer tube 312. The outer tube 312 can be, for example, a glass or stainless steel coil having a length of about 1 meter to about 5 meters, and an inner diameter of less than about 1 mm. The stationary phase 314 within the outer tube 312 can be diatomite coated or bonded with methylpolysiloxane. However, the tube 312 and the stationary phase 314 can be made of any suitable materials and have any suitable dimensions as known in the art for their intended purposes.

With further reference to FIG. 2, the injection port can be, for example, a programmable temperature vaporizer fluidly coupled with the interior of the column. However, the disclosed subject matter is not limited to programmable injection ports. Any injection port capable of being heated to suitable temperatures separately from the column can be used in accordance with the disclosed subject matter. In addition, in some analyzers, it is possible to inject or deposit the sample directly into the column. With such an arrangement, the injection port and column are one.

With further reference to FIG. 2, the analyzer can also include a reservoir 210 of carrier gas in fluid communication with the injection port 202. The carrier gas can be used to direct a vaporized sample from the injection port 202 into the column 204. The carrier gas can be, for example, helium, nitrogen, argon, or hydrogen. The carrier gas reservoir 210 can be coupled to the injection port and column via a valve 212.

With reference again to FIG. 1, a sample can be introduced into the injection port. In accordance with an exemplary embodiment of the disclosed subject matter, the sample can be a petroleum sample. For example, the sample can be residua or a petroleum stream including a high concentration of residua. However, those of skill in the art will understand that the disclosed subject matter is not limited to use with a petroleum sample. Other samples that require simdis can include, for example, fractions isolated from petroleum residua either by separation techniques like liquid chromatography or samples from processing of the petroleum sample into other products, feedstocks used in chemical processing, additives etc.

Figure 9:
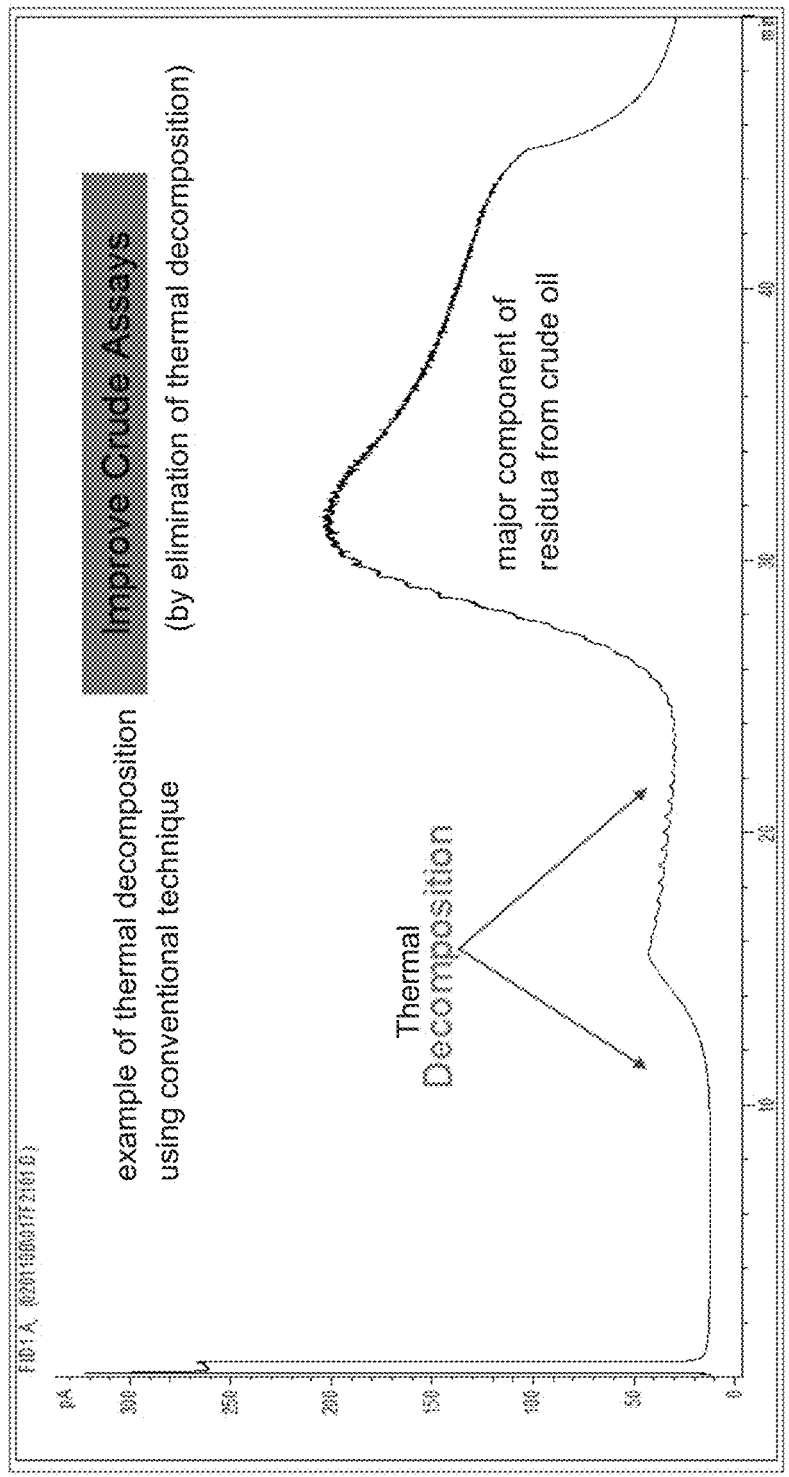
FIG. 9 shows a gas chromatogram of residua from a crude oil assay procedure using conventional HT-simdis which exhibits thermal decomposition.

FIG. 9 illustrates an example of how the disclosed subject matter can improve the assay of crude oils by providing accurate boiling point profiles to generate a full crude assay distillation curve by eliminating the decomposition 'hump' of a residua cut which would make the petroleum erroneously appear to initiate boiling point at a much lower temperature. Such decomposition would be present not only with the residua cut but also with a whole uncut crude oil subjected to a full boiling point analysis by HT-simdis.

Figure 10:
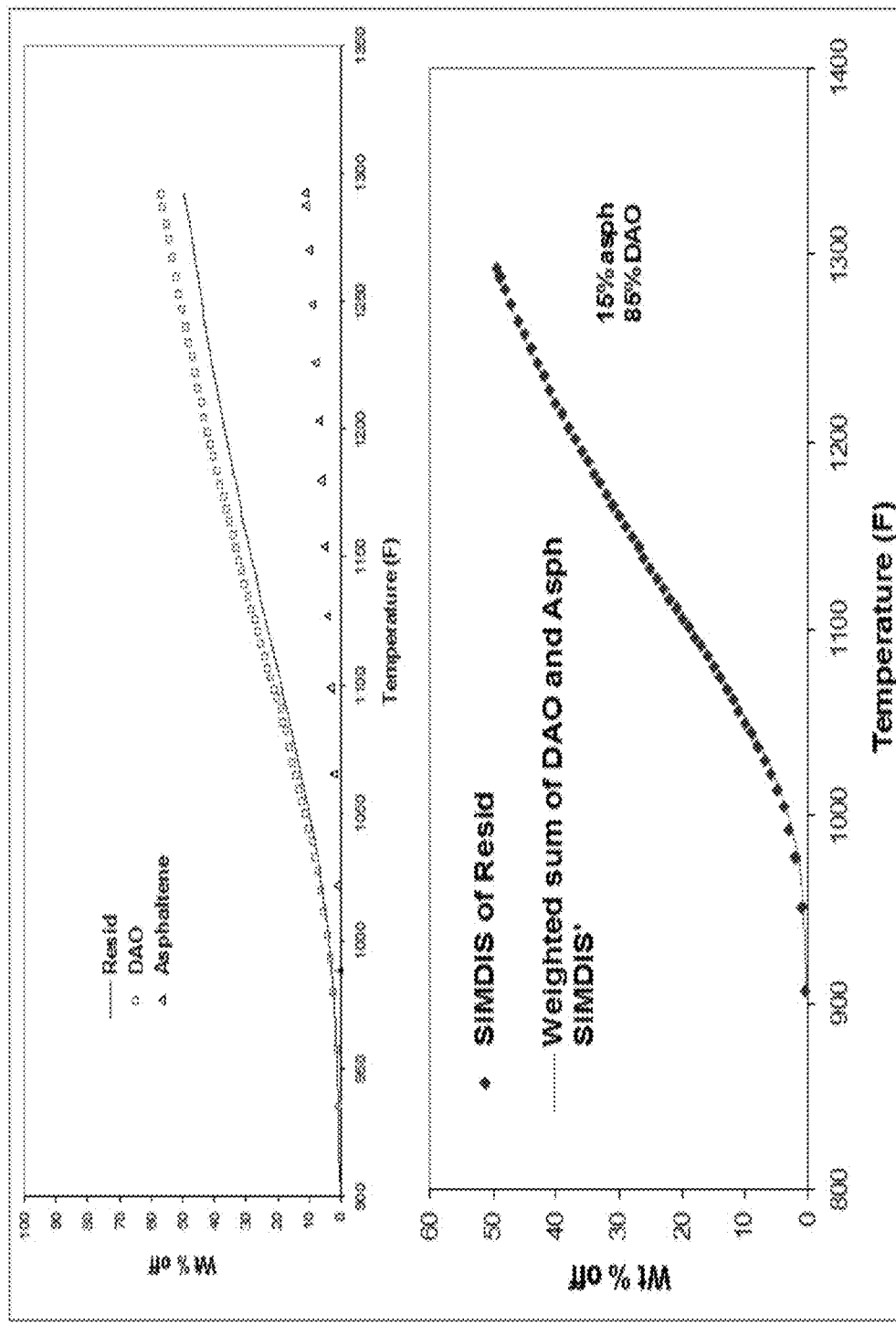
FIG. 10 is an example of accurate boiling point curves of residua processing generated in accordance with an exemplary embodiment of the disclosed subject matter.

FIG. 10 illustrates the improved distillation curves using the disclosed subject matter for a refining processing in which a residua is converted into two components of a deasphalted oil (DAO) and asphaltene. The sum of the HT-simdis curves of the DAO and asphaltene when combined yield exactly the simdis curve of the original residua from which the two components originated.

Figure 4A:
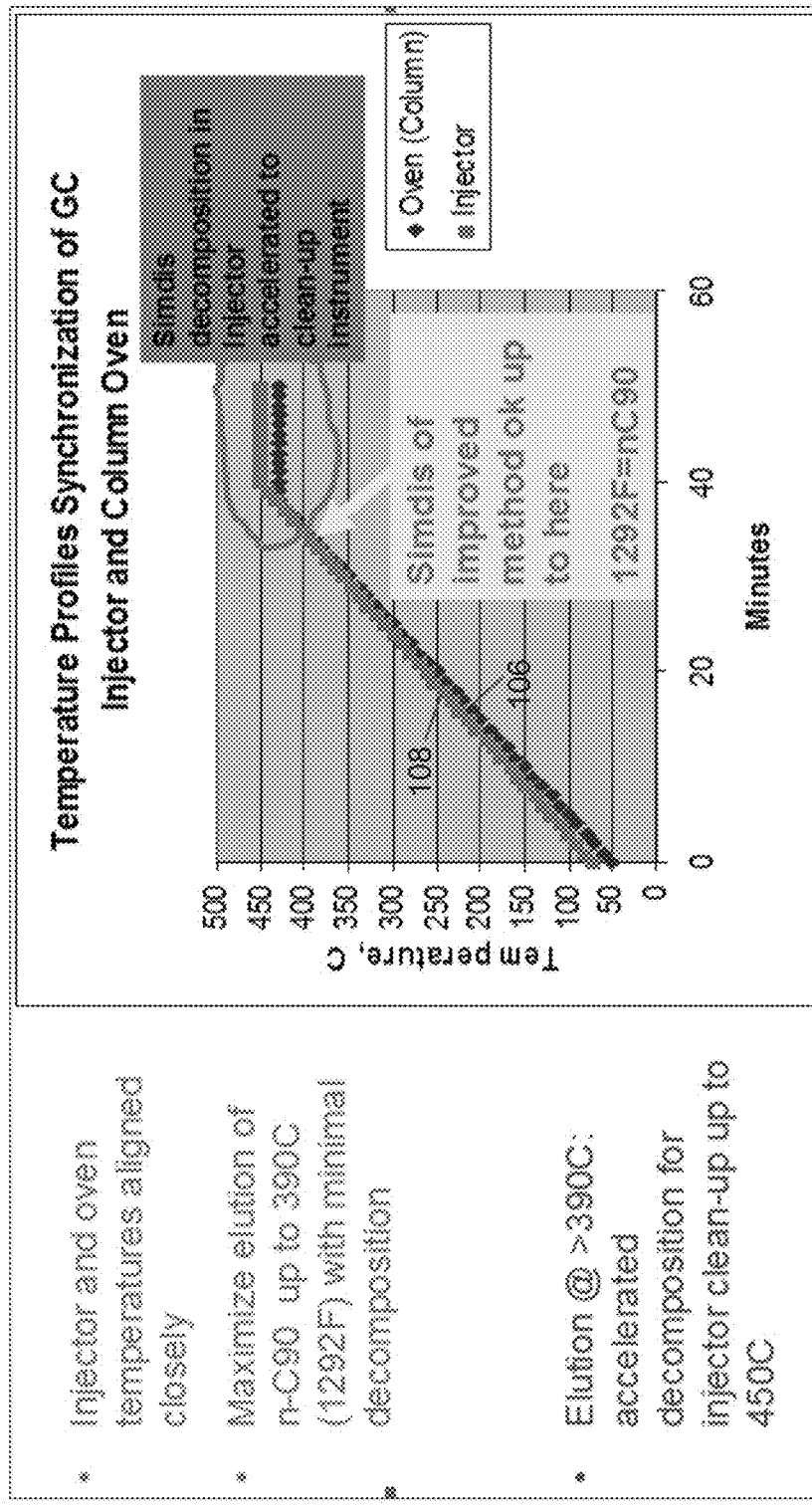
FIG. 4A is a graph illustrating a representative temperature ramp for the column and injection port in accordance with the disclosed subject matter.

In accordance with the disclosed subject matter, and with further reference to FIG. 4A1, the temperature of the column is increased at a first rate at 106. For example, and not limitation, the temperature of the column can start at an initial column temperature and increase at a constant rate. The rate can vary based on a number of factors, including the characteristics of the heating elements. For example, the initial column temperature can be about −20° C., about 0° C., about 20° C., about 30° C., about 40° C., about 50° C., about 60° C., about 70° C., or about 80° C., and the temperature of the column can increase at a rate of about 3° C./min, about 4° C./min, about 5° C./min, about 6° C./min, about 7° C./min, about 8° C./min, about 9° C./min, about 10° C./min, about 11° C./min, about 12° C./min, about 13° C./min, about 14° C./min, or about 15° C./min or 20° C./min or 40° C./min or greater or equal to greater than 100° C./min (e.g. as in ultra fast gas chromatography). Alternatively, the temperature of the column can be increased in a non-uniform manner (exponentially, or at a non-constant rate).

In accordance with another aspect of the disclosed subject matter, and with further reference to FIG. 4A, the temperature of the injection port can be increased at a second rate at 108. The second rate can be the same as the first rate. Alternatively, the second rate can be different than the first rate. For example, and not limitation, the temperature of the injection port can start at an initial injection port temperature and increase at a constant rate. The rate can vary based on a number of factors, including the initial starting temperature, characteristics of the heating elements and the desired HT-simdis application. The initial temperature of the injection port can vary. For example, the initial injection port temperature can be about 40° C., about 50° C., about 60° C., about 70° C., about 80° C., about 90° C., about 100° C., and can increase at a rate of about 2.5° C./min, about 3.5° C./min, about 4.5° C./min, about 5.5° C./min, about 6.5° C./min, about 7.5° C./min, about 8.5° C./min, about 9.5° C./min, about 10.5° C./min, about 11.5° C./min, about 12.5° C./min, about 13.5° C./min, or about 14.5° C./min or higher rates as in ultra-fast gas chromatography. Alternatively, and as noted above in connection with regard to the column temperature, the temperature of the injection port can be increased in non-uniform manner (i.e., exponentially or at a non-constant rate).

In accordance with the disclosed subject matter, however, the rate of temperature increase for the injection port and the rate of temperature increase of the column are selected such that the temperature of the injection port is within approximately equal to, e.g., within about five to fifteen degrees Celsius, to the temperature of the column at a target temperature. The temperature of the injection port is preferably within five to ten degrees Celsius of the temperature of the column. The temperature of the injection port is more preferably within five degrees Celsius of the temperature of the column. The temperature of the injection port is more preferably equal to the temperature of the column. Essentially, the closer the injection port temperature is to column temperature when the target temperature is reached without compromising chromatographic performance, the more accurate the simdis result. The target temperature can be approximately the temperature at which thermal decomposition begins. For example, the target temperature can be the temperature at which thermal decomposition begins, a temperature slightly above the temperature at which thermal decomposition begins, or a temperature slightly below the temperature at which thermal decomposition begins. For example, and with reference to an illustrative embodiment wherein the sample is a petroleum sample, the target temperature can be between about 380° C. and about 400° C., between about 385° C. and about 395° C., between about 386° C. and 391° C., or between about 389° C. and about 390° C. For example, the target temperature can be about 380° C., about 382° C., about 384° C., about 385° C., about 387° C., about 388° C., about 389° C., about 390° C., about 391° C., about 392° C., about 393° C., about 394° C., about 395° C., about 396° C., about 398° C., or about 400° C.

As used herein, approximately equal means that the temperature of the injection port is within about 5 to 15 degrees Celsius of the temperature of the column when the temperature of the injection port and/or the temperature of the column reach the target temperature. For example, approximately equal can mean the temperature of the injection port can be within about 4° C., within about 3° C., within about 2.5° C., within about 2° C., within about 1.5° C., within about 1° C., within about 0.5° C., or even the same as the temperature of the column.

Figure 4B:
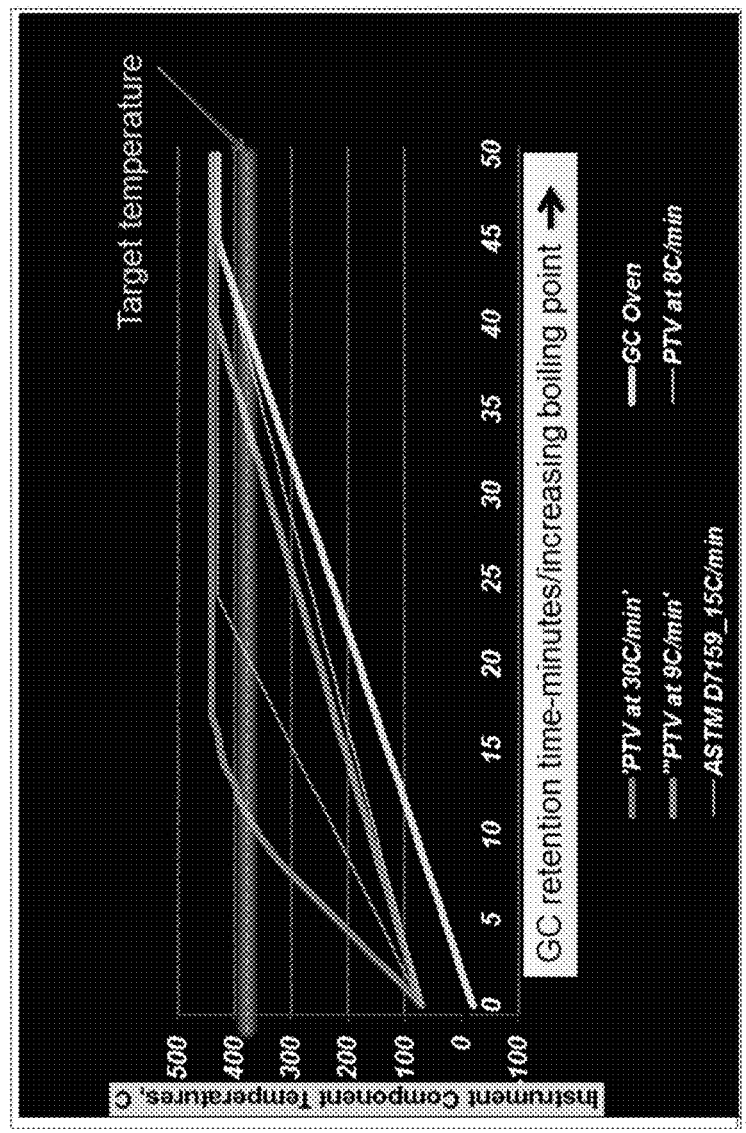
FIG. 4B further illustrating the problem resolved with the disclosed subject matter.

As illustrated in FIG. 4B, using significant faster injection port temperature rate versus column temperature results in the injection port temperature reaching the target temperature much earlier, thus leading to appearance of decomposition components at much lower boiling point signal. By slowing the injection port temperature rate to reach the target temperature at approximately the same time as the column temperature reaching the target temperature leads to a creation of a much wider decomposition free boiling point range that can be used to obtain more accurate simdis results. It should be noted that conventional temperature rate as recommended in the conventional ASTM HT-simdis test method D7169 would lead to reaching the target temperature also much earlier and thus lead to an inaccurate simdis boiling point curve of the samples.

To achieve the comportive target rates, herein, injection port heating element 206 and column heating element 208 can be coupled to a process including one or more electronic circuits for controlling the temperature ramp. For example, the system can include a non-transitory computer readable medium containing instructions that, when implemented, will cause the one or more processors to control the temperature ramps of the injection port 202 and the column 204 using the injection port heating element 206 and the column heating element 208. Control of the injection port heating element 206 and the column heating element 208 can be implemented using hardware, software, or a combination thereof. However, those having ordinary skill in the art will understand that even in a pure software implementation of the appropriate instructions, one or more processors is required to implement the instructions.

In accordance with another aspect of the disclosed subject matter, and with further reference to FIG. 2, the analyzer as embodied can include a detector 214. The detector 214 is located at a location on the column 204 remote from the injection port 202 to provide a quantitative measurement of the components of the sample eluted in combination with the carrier gas. For example, with the injection port located proximate one end of the column, such as near or at the location of the front of the column, the detector can be located proximate the opposite end of the column. The detector can be, for example, a mass spectrometry detector, a flame ionization detector, an electron-capture detector, an atomic emission detector, a chemiluminescence detector, or a photoionization detector or other detection systems that are adaptable to the simdis analysis for hydrocarbons and hetero atoms containing streams, such as O, S, N, F, Cl, Ni, V, etc.

Figure 5:
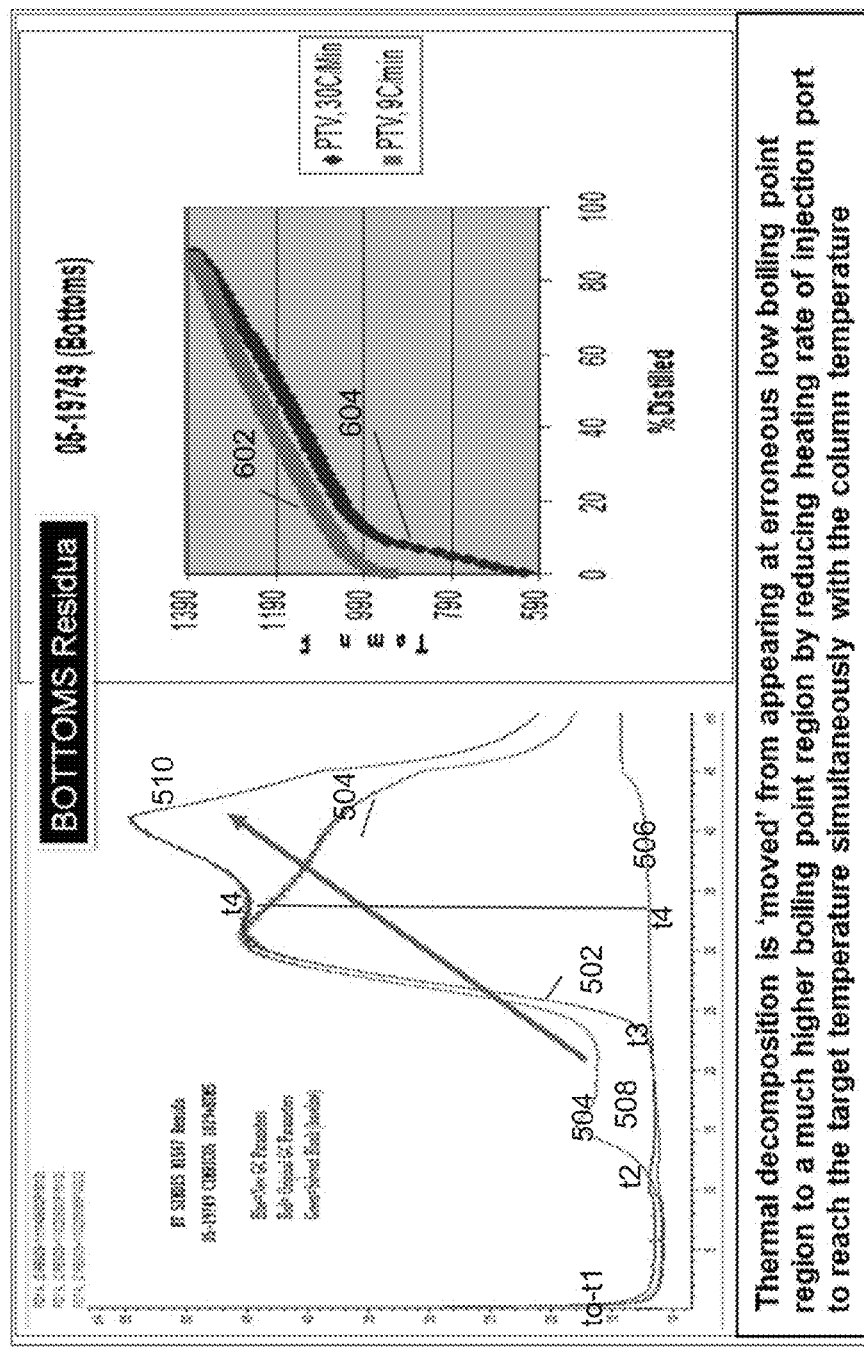
FIG. 5 illustrates the comparison between an embodiment of the disclosed subject matter and a conventional method when applied to the bottoms fraction, wherein the left side of FIG. 5 is a gas chromatogram comparing the results of gas chromatography using an embodiment of the disclosed subject matter versus the results of gas chromatography using a conventional method and the results of gas chromatography using a solvent, and the right side of FIG. 5 is a graph comparing the results of the distillation curve using an embodiment of the disclosed subject matter versus the distillation curve using a conventional method.

A comparison between a gas chromatography measurement in accordance with the disclosed subject matter and a gas chromatography measurement in accordance with conventional methods is shown in FIG. 5. The gas chromatography measurement in accordance with the disclosed subject matter is shown at 502. The gas chromatography measurement in accordance with conventional methods, i.e., wherein the temperature of the injection port is not approximately equal to the temperature of the column at a target temperature, is shown at 504. In particular, the gas chromatography shown at 504 corresponds with a conventional method in which the temperature of the injection port is significantly greater than the temperature of the column when the temperature of the injection port reaches the target temperature. The measurements of a solvent are shown at 506 in order to establish a baseline.

As shown in FIG. 5, when the temperature of the column and the temperature of the injection port are initially raised, respectively, the measurements remain at zero because none of the sample will elute at such low temperatures. Thus, the measurements utilizing the disclosed subject matter, the conventional methods, and the solvent will appear the same from $t_0$ to $t_1$. Likewise, between times $t_1$ and $t_2$, the temperatures are still too low for any of the sample to elute, as reflected in the measurements using the disclosed subject matter and the solvent. However, the measurement of the sample using the conventional method shows a peak at 508. This peak does not reflect the true state of the elution and thus will have a negative effect on the results of the analysis, such that the boiling point distribution cannot be calculated correctly. Although not bound by any particular theory, the peak at 508 is understood to be a reflection of the onset of thermal cracking, resulting from the injection port temperature reaching a thermal decomposition temperature significantly ahead of the column temperature. Thus, the effects of thermal decomposition using a conventional technique will cause inaccuracies.

Rather, and in accordance with the disclosed subject matter, data representative of the sample embodied herein begins at approximately time $t_3$. From time $t_3$ to time $t_4$, accurate data can be obtained and used to calculate the boiling point distribution of the sample. However, the observed maximum decomposition free analyzer injection port and column temperature is approximately 390° C. An analyzer temperature of 390° C. corresponds, under the column dimensions and operating conditions used in the example, to about 1292° F. (700° C.) which is equivalent to the boiling point of n-$C_{90}$. Therefore, data at analyzer injection port and/or column temperatures above approximately 390° C. will be affected by thermal decomposition regardless of how the process is performed. It may be possible that the decomposition free boiling point $t_3$ to $t_4$ range of n-$C_{90}$ (or 1292° F. equivalent) may be extended slightly higher while using some variation in the simdis operating conditions. For example, a shorter column and thinner column inner phase coating may elute heavier compounds at a slightly lower analyzer injector/column temperatures. In any case, an analyzer temperature of 390° C. appears to be the maximum temperature before on-set of thermal decomposition for many resid samples.

Thus, and in accordance with yet another aspect of the disclosed subject matter, the data obtained after time t4 can generally be discarded. Note that the data after $t_4$ using the technique of the disclosed subject matter includes a peak at 510 corresponding to the shifting of peak 508 to a much longer time and thus a higher boiling point range. In contrast, in accordance with the disclosed subject matter, a larger amount of accurate data can be gathered by shifting the thermal decomposition to a much longer analyzer run time.

In view of the above, and as described herein, a cutoff temperature can be defined. The cutoff temperature can be defined prior to the measurements or after the measurements. The cutoff temperature can be, for example, a target temperature. All data gathered at temperatures higher than the cutoff temperature can be discarded, and the remaining data can be used to calculate a detailed simdis report up to the target temperature and the total amount of the sample that has a boiling point greater than the target cut-off temperature can also be calculated using any suitable techniques known in the art for its intended purpose. For example, the amount of material boiling above the boiling point of n-$C_{90}$ can be determined with a quantitative calibration standard.

With reference to right side of FIG. 5, for purpose of illustration and not limitation, distillation curves for the disclosed subject matter and the conventional method are shown at 602 and 604, respectively. As shown, the sample in the conventional method begins distillation well below the temperature that would be expected. In contrast, the sample in accordance with the disclosed subject matter demonstrates no distillation until further temperatures.

Figure 6:
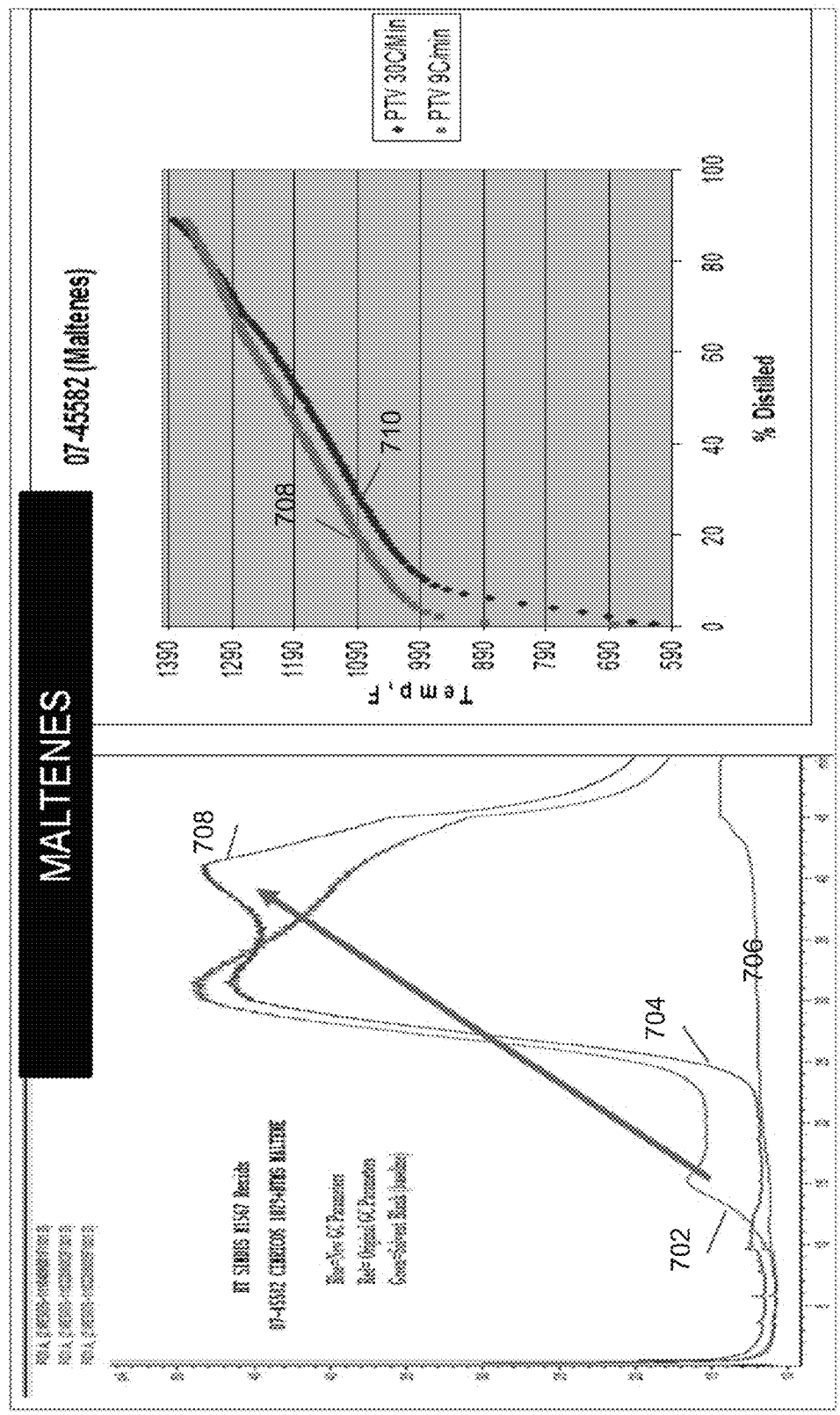
FIG. 6 illustrates the comparison between an embodiment of the disclosed subject matter and a conventional method when applied to the maltene fraction (e.g., the fraction remaining after most of the 'asphaltene' components are removed by solvent solubility), wherein the left side of FIG. 6 is a gas chromatogram comparing the results of gas chromatography using an embodiment of the disclosed subject matter versus the results of gas chromatography using a conventional method and the results of gas chromatography using a solvent, and the right side of FIG. 6 is a graph comparing the results of the distillation curve using an embodiment of the disclosed subject matter versus the distillation curve using a conventional method.

For purposes of illustration, FIG. 6 shows an HT-Simdis chromatogram of a maltene fraction. The maltene fraction was isolated from the residua. The left side of FIG. 6 shows the results of gas chromatography using an embodiment of the disclosed subject matter (at 704), the results of gas chromatography using conventional methods (at 702), and the results of gas chromatography using a solvent (at 706). The right side of FIG. 6 shows a graph comparing the results of the distillation curve over time using an embodiment of the disclosed subject matter (at 708) versus the distillation curve over time using conventional methods (at 710). Similar to the HT-Simdis chromatogram shown in FIG. 5, the maltene fraction in accordance with the disclosed subject matter shows a peak 708 associated with the significant thermal decomposition that can occur in accordance with the conventional methods at 702. In contrast, the disclosed subject matter at 704 shows no such peak until after the boiling point of n-$C_{90}$. As before, a solvent at 706 is shown for purposes of comparison.

Figure 7:
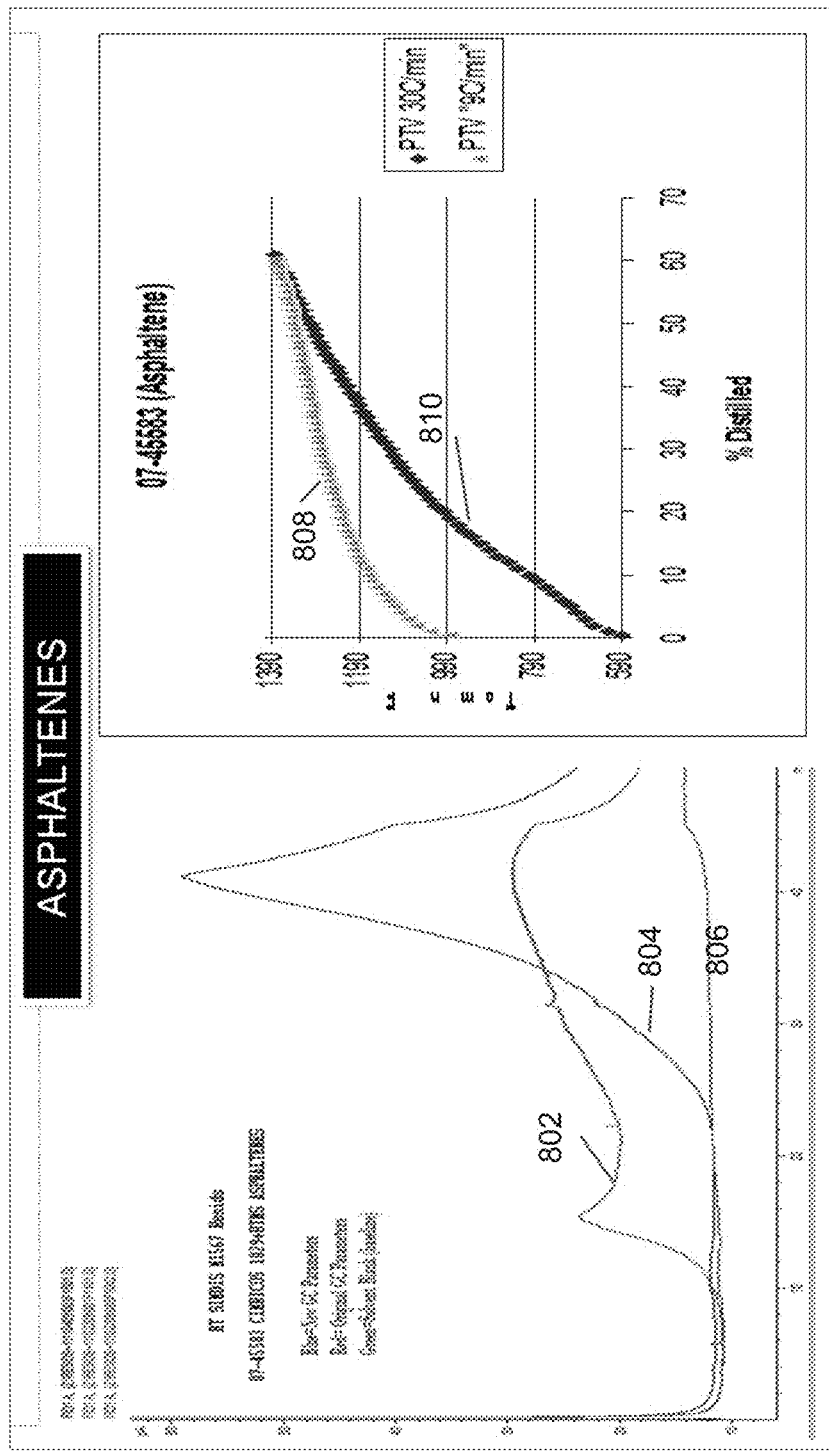
FIG. 7 illustrates the comparison between an embodiment of the disclosed subject matter and conventional methods when applied to the asphaltenes fraction of the residua, wherein the left side of FIG. 7 is gas chromatogram comparing the results of gas chromatography using an embodiment of the disclosed subject matter versus the results of gas chromatography using a conventional method and the results of gas chromatography using a solvent, and the right side of FIG. 7 is a graph comparing the results of the distillation curve using an embodiment of the disclosed subject matter versus the distillation curve using a conventional method.
Figure 8:
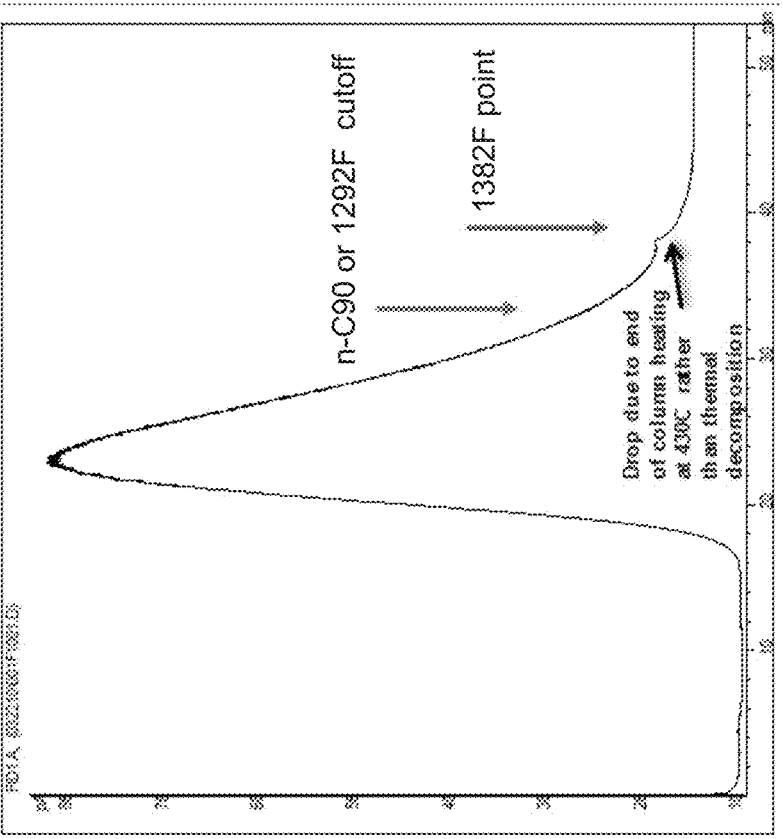
FIG. 8 shows a gas chromatogram for saturated hydrocarbon fraction (e.g. obtained from a liquid chromatographic separation of the maltene fraction) generated in accordance with an exemplary embodiment of the disclosed subject matter.

A similar chart is shown in FIG. 7. In particular, the left side of FIG. 7 shows the results of gas chromatography using an embodiment of the disclosed subject matter (at 804), the results of gas chromatography using conventional methods (at 802), and the results of gas chromatography using a solvent (at 806), and the right side of FIG. 7 shows a graph comparing the results of the distillation curve over time using an embodiment of the disclosed subject matter (at 808) versus the distillation curve over time using conventional methods (at 810).

FIG. 9 shows the HT-Simdis chromatogram for a saturated (e.g. parafins and cycloparafins) hydrocarbon fraction isolated from a residua by the well known liquid chromatography procedure. This saturates fraction is relatively stable thermally and exhibits little to no decomposition. The saturates are eluted by approximately carbon number up to approximately $C_{120}$ range. For the saturate fraction, a boiling point distribution may be possible up to approximately 1382° F. versus the 1232° F. of the others due to higher thermal stability compared to the other fractions. The systems and methods of the disclosed subject matter can be directed to alternative fractions.

In accordance with a further aspect of the disclosed subject matter, the temperature of the injection port and column can continue to be increased to a higher temperature past the target cut-off temperature to elute the remaining portions of the sample. This can be used, for example, to clean the injector and column. In addition, one or more blank runs can be used to further clean the injection port and the column. For example, three or four blank runs can be used if necessary before the analysis of the next sample.

With further reference to FIG. 2, the information gathered by detector 214 can be communicated to one or more computation units. The one or more computation units can be programmed to carry out a number of analytical methods as known in the art. For example, computation units can be programmed to calculate the boiling point distribution of the sample based on the received data and/or to construct a Heavy Hydrocarbon Model of Composition for the sample. The one or more computation units can be implemented as hardware, software, or a combination thereof. However, it is required that even in a pure software implementation, one or more processors will be used to implement the instructions contained in software. The one or more processors include one or more electronic circuits. The computation units can also be used for crude assays. In addition to residua fractions, the technique presented is applicable to a wide range of petroleum fractions that contain high boiling components. Some of these include all types of crude oils, oil derived from oil sands, condensates, pyrolysis products, etc.

ADDITIONAL EMBODIMENTS

Additionally or alternatively, the invention can include one or more of the following embodiments.

Embodiment 1

A method for determining a boiling point distribution of a sample, the method comprising providing an analyzer including a column comprising a column heating element and an injection port coupled to the column, the injection port comprising an injection port heating element, introducing a sample into the injection port, raising a temperature of the column at a first rate using the column heating element, and raising a temperature of the injection port at a second rate using the injection port heating element, wherein the first rate and the second rate are selected such that the temperature of the injection port is within five to fifteen degrees Celsius of the temperature of the column when the temperature of the column reaches a target temperature.

Embodiment 2

The method of Embodiment 1, wherein the column comprises a wall coated open tubular column.

Embodiment 3

The method of Embodiment 1, wherein the column comprises a packed column.

Embodiment 4

The method of any of the previous Embodiments, wherein the injection port comprises a programmable temperature vaporizer or injector is part of the column.

Embodiment 5

The method of any of the preceding Embodiments, wherein the target temperature is between about 380° C. and about 400° C.

Embodiment 6

The method of any of the preceding Embodiments, wherein the target temperature is about 390° C.

Embodiment 7

The method of any of the preceding Embodiments, wherein the temperature of the injection port is higher than the temperature of the column when the temperature of the injection port reaches the target temperature.

Embodiment 8

The method of any of the preceding Embodiments, wherein the temperature of the column is lower than the temperature of the injection port when the temperature of the injection port reaches the target temperature.

Embodiment 9

The method of any of the preceding Embodiments, wherein the first rate is greater or lower than the second rate.

Embodiment 10

The method of any of the preceding Embodiments, wherein a starting temperature of the column is lower or equal than a starting temperature of the injection port.

Embodiment 11

The method of any of the preceding Embodiments, further comprising measuring a boiling point distribution of the sample.

Embodiment 12

The method of Embodiment 11, further comprising defining a cutoff temperature and selecting a first set of data associated with temperatures lower than the cutoff temperature to measure the boiling point distribution of the sample.

Embodiment 13

The method of Embodiment 12, wherein the cutoff temperature is the target temperature.

Embodiment 14

The method of Embodiment 12, wherein the cutoff temperature is lower than the target temperature.

Embodiment 15

The method of any of Embodiments 12, 13, or 14, wherein the first set of data is below the cutoff temperature.

Embodiment 16

The method of any of the preceding Embodiments, wherein the sample comprises a petroleum stream.

Embodiment 17

The method of Embodiment 16, further comprising constructing an initial estimate of a composition of the petroleum stream.

Embodiment 18

The method of Embodiment 17, wherein constructing the initial estimate of the composition of the petroleum stream comprises using mass spectrometry.

Embodiment 19

The method of Embodiment 17, wherein constructing the initial estimate of the composition of the petroleum stream comprises using one of a flame ionization detector, a mass spectrometer and other element selective detectors.

Embodiment 20

The method of Embodiments 17, 18, or 19, wherein constructing the initial estimate of the composition of the petroleum stream comprises constructing a Heavy Hydrocarbon Model of Composition.

Embodiment 21

The method of any of the preceding Embodiments, further comprising creating a chromatogram based on an analysis of the sample.

Embodiment 22

The method of any of the preceding Embodiments, further comprising continuing to raise the temperature of the column after the temperature of the injection port reaches a target temperature to elute remaining portions of the sample.

Embodiment 23

The method of any of the preceding Embodiments, wherein the first rate and the second rate are selected such that the temperature of the injection port is within five to ten degrees Celsius of the temperature of the column when the temperature of the column reaches a target temperature.

Embodiment 24

The method of any one of the preceding Embodiments, wherein the first rate and the second rate are selected such that the temperature of the injection port is within five degrees Celsius of the temperature of the column when the temperature of the column reaches a target temperature.

Embodiment 25

A system for determining a boiling point distribution of a sample, the system comprising an analyzer including a column heating element and an injection port coupled to the column, the injection port comprising an injection port heating element, wherein the analyzer is configured to raise a temperature of the injection port at a second rate using the injection port heating element, wherein the first rate and the second rate are selected such that that temperature of the injection port is within five to fifteen degrees Celsius of the temperature of the column when the temperature of the column reaches a target temperature.

Embodiment 26

The system according to Embodiment 24, wherein the first rate and the second rate are selected such that the temperature of the injection port is within five to ten degrees Celsius of the temperature of the column when the temperature of the column reaches a target temperature.

Embodiment 27

The system according to Embodiment 24 or Embodiment 25, wherein the first rate and the second rate are selected such that the temperature of the injection port is within five degrees Celsius of the temperature of the column when the temperature of the column reaches a target temperature.

While the present application is described herein in terms of certain preferred embodiments, those skilled in the art will recognize that various modifications and improvements may be made to the application without departing from the scope thereof. Thus, it is intended that the present application include modifications and variations that are within the scope of the appended claims and their equivalents. Moreover, although individual features of one embodiment of the application may be discussed herein or shown in the drawings of one embodiment and not in other embodiments, it should be apparent that individual features of one embodiment may be combined with one or more features of another embodiment or features from a plurality of embodiments.

In addition to the specific embodiments claimed below, the application is also directed to other embodiments having any other possible combination of the dependent features claims below and those disclosed above. As such, the particular features presented in the dependent claims and disclosed above can be combined with each other in other manners within the scope of the application such that the application should be recognized as also specifically directed to other embodiments having any other possible combinations. Thus, the foregoing description of specific embodiments of the application has been presented for purposes of illustration and description. It is not intended to be exhaustive or to limit the application to those embodiments disclosed.

What is claimed is:

1. A method for determining a boiling point distribution of a sample, the method comprising:
    providing an analyzer comprising:
        a column comprising a column heating element; and
        an injection port coupled to the column, the injection port comprising an injection port heating element;
    introducing a sample into the injection port;
    raising a temperature of the column at a first rate using the column heating element;
    raising a temperature of the injection port at a second rate using the injection port heating element,
    wherein the first rate and the second rate are selected such that the temperature of the injection port is within about fifteen degrees Celsius of the temperature of the column when the temperature of the column reaches a target temperature;
    eluting the sample in the column into components; and
    measuring a boiling point distribution of the sample,
    wherein measuring the boiling point distribution includes defining a cutoff temperature, using a detector to provide quantitative measurements of the components eluted in the column, and selecting a first set of data of quantitative measurements associated with temperatures lower than the cutoff temperature to measure the boiling point distribution of the sample.

2. The method of claim 1, wherein the column comprises a wall coated open tubular column.

3. The method of claim 1, wherein the column comprises a packed column.

4. The method of claim 1, wherein the injection port comprises a programmable temperature vaporizer.

5. The method of claim 1, wherein the target temperature is about 390° C.

6. The method of claim 1, the temperature of the injection port is higher than the temperature of the column when the temperature of the injection port reaches a target temperature.

7. The method of claim 1, wherein the first rate is lower, greater or equal than the second rate.

8. The method of claim 4, wherein a starting temperature of the column is lower than a starting temperature of the injection port.

9. The method of claim 1, wherein the cutoff temperature is the target temperature.

10. The method of claim 1, wherein the cutoff temperature is lower than the target temperature.

11. The method of claim 1, wherein the first set of data comprises all data gathered when the temperature of the injection port is below or equal the cutoff temperature.

12. The method of claim 1, wherein the sample comprises a petroleum stream.

13. The method of claim 12, further comprising constructing an estimate of a composition of the petroleum stream using the first set of data.

14. The method of claim 13, wherein constructing the estimate of the composition of the petroleum stream comprises using mass spectrometry.

15. The method of claim 13, wherein constructing the estimate of the composition of the petroleum stream comprises using one of a flame ionization detector, or a mass spectrometer and other element selective detectors.

16. The method of claim 13, wherein constructing the estimate of the composition of the petroleum stream comprises constructing a Heavy Hydrocarbon Model of Composition.

17. The method of claim 1, further comprising creating a chromatogram based on an analysis of the sample.

18. The method of claim 1, further comprising continuing to raise the temperature of the column and injection port after the temperature of the injection port and column are within 15 degrees C. of each other when reaching the target temperature to a temperature sufficient to elute remaining portions of the sample.

19. The method of claim 1, wherein the first rate and the second rate are selected such that the temperature of the injection port is within five to ten degrees Celsius of the temperature of the column when the temperature of the column reaches a target temperature.

20. The method of claim 1, wherein the first rate and the second rate are selected such that the temperature of the injection port is within five degrees Celsius of the temperature of the column when the temperature of the column reaches a target temperature.

* * * * *